(12) United States Patent
Yang (10) Patent No.: US 12,280,240 B2
(45) Date of Patent: Apr. 22, 2025

(54) UNILATERAL-DRIVEN DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 790 days.

(21) Appl. No.: 17/622,242

(22) PCT Filed: Jun. 22, 2020

(86) PCT No.: PCT/CN2020/097319
§ 371 (c)(1),
(2) Date: Dec. 23, 2021

(87) PCT Pub. No.: WO2021/012853
PCT Pub. Date: Jan. 28, 2021

(65) Prior Publication Data
US 2022/0347380 A1    Nov. 3, 2022

(30) Foreign Application Priority Data

Jul. 19, 2019  (WO) ................ PCT/CN2019/096673
Dec. 31, 2019  (WO) ................ PCT/CN2019/130442
Dec. 31, 2019  (WO) ................ PCT/CN2019/130445

(51) Int. Cl.
*A61M 5/172*   (2006.01)
*A61B 5/00*    (2006.01)
(Continued)

(52) U.S. Cl.
CPC ....... *A61M 5/1723* (2013.01); *A61B 5/14532* (2013.01); *A61B 5/1473* (2013.01);
(Continued)

(58) Field of Classification Search
CPC ............ A61M 5/1723; A61M 5/14236; A61M 5/14244; A61M 5/14248; A61M 5/1452;
(Continued)

(56) References Cited

U.S. PATENT DOCUMENTS

2003/0236498 A1   12/2003  Gross et al.
2009/0099521 A1   4/2009   Gravesen et al.
(Continued)

FOREIGN PATENT DOCUMENTS

CN    103260678    8/2013
CN    103463695    12/2013
(Continued)

OTHER PUBLICATIONS

"International Search Report (Form PCT/ISA/210) of PCT/CN2020/097319" mailed on Sep. 14, 2020, pp. 1-4.
(Continued)

*Primary Examiner* — Tasnim Mehjabin Ahmed
(74) *Attorney, Agent, or Firm* — JCIP GLOBAL INC.

(57) ABSTRACT

A unilateral-driven drug infusion device includes a drug storage unit, a screw, at least one driving unit, a power unit, a reset unit and an infusion tube. The drug storage unit includes a drug outlet. The screw is connected to a piston and a driving wheel provided with wheel teeth, respectively, wherein the driving wheel drives the screw to move by rotation, and push the piston provided in the drug storage unit to move forward. The driving unit cooperates with the driving wheel, wherein the driving unit includes at least one driving portion. The power unit and the reset unit are connected to the driving unit. The infusion tube includes a connection end and a subcutaneous end, and the connection end is communicated with the drug outlet and the subcutaneous end.

14 Claims, 7 Drawing Sheets

(51) Int. Cl.
| | |
|---|---|
| A61B 5/145 | (2006.01) |
| A61B 5/1473 | (2006.01) |
| A61F 2/02 | (2006.01) |
| A61M 5/142 | (2006.01) |
| A61M 5/145 | (2006.01) |
| A61M 5/158 | (2006.01) |
| G16H 20/17 | (2018.01) |
| G16H 40/63 | (2018.01) |
| A61M 5/14 | (2006.01) |
| A61M 5/20 | (2006.01) |

(52) U.S. Cl.
CPC ............ *A61B 5/4839* (2013.01); *A61F 2/022* (2013.01); *A61M 5/14236* (2013.01); *A61M 5/14244* (2013.01); *A61M 5/14248* (2013.01); *A61M 5/1452* (2013.01); *A61M 5/1454* (2013.01); *A61M 5/158* (2013.01); *A61M 5/172* (2013.01); *G16H 20/17* (2018.01); *G16H 40/63* (2018.01); *A61B 2560/0209* (2013.01); *A61B 2562/043* (2013.01); *A61M 5/1413* (2013.01); *A61M 2005/14208* (2013.01); *A61M 2005/14252* (2013.01); *A61M 2005/14268* (2013.01); *A61M 2005/14506* (2013.01); *A61M 2005/1585* (2013.01); *A61M 2005/1726* (2013.01); *A61M 2005/2006* (2013.01); *A61M 2205/0216* (2013.01); *A61M 2205/0233* (2013.01); *A61M 2205/0266* (2013.01); *A61M 2205/33* (2013.01); *A61M 2205/3317* (2013.01); *A61M 2205/3327* (2013.01); *A61M 2205/3553* (2013.01); *A61M 2205/3576* (2013.01); *A61M 2205/3592* (2013.01); *A61M 2205/50* (2013.01); *A61M 2205/502* (2013.01); *A61M 2209/088* (2013.01); *A61M 2230/005* (2013.01); *A61M 2230/20* (2013.01); *A61M 2230/201* (2013.01)

(58) Field of Classification Search
CPC .... A61M 5/1454; A61M 5/158; A61M 5/172; A61B 5/14532; A61B 5/1473; A61B 5/4839
See application file for complete search history.

(56) References Cited

U.S. PATENT DOCUMENTS

| | | | |
|---|---|---|---|
| 2012/0004620 A1* | 1/2012 | Spool | A61M 5/24 604/207 |
| 2019/0117881 A1 | 4/2019 | Yang | |

FOREIGN PATENT DOCUMENTS

| | | |
|---|---|---|
| CN | 105311705 | 2/2016 |
| CN | 106110445 | 11/2016 |
| CN | 206045102 | 3/2017 |
| EP | 1987855 | 11/2008 |

OTHER PUBLICATIONS

"Search Report of Europe Counterpart Application", issued on Jul. 31, 2023, p. 1-p. 7.

* cited by examiner

UNILATERAL-DRIVEN DRUG INFUSION DEVICE

CROSS-REFERENCE TO RELATED APPLICATION

This application is a 371 of international application of PCT application serial no. PCT/CN2020/097319, filed on Jun. 22, 2020, which claims the priority benefit of PCT application no. PCT/CN2019/096673 field on Jul. 19, 2019, PCT application no. PCT/CN2019/130445 filed on Dec. 31, 2019, and PCT application no. PCT/CN2019/130442 field on Dec. 31, 2019. The entirety of each of the above mentioned patent applications is hereby incorporated by reference herein and made a part of this specification.

TECHNICAL FIELD

The present invention mainly relates to the field of medical instruments, in particular to a unilateral-driven drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The existing drug infusion device, controlled by remote device, is usually attached directly on the patient's skin through a medical adhesive tape.

At present, the infusion device in prior art is prone to drug blockage during use, and the drug cannot be infused into the body in time, which affects the user's health and has potential safety hazards.

Therefore, the prior art urgently needs a drug infusion device that is not easily blocked.

BRIEF SUMMARY OF THE INVENTION

Embodiments of the present invention disclose a unilateral-driven drug infusion device in which the power unit drives the driving portion to push the wheel teeth forward. By controlling the current, the power unit can output a sufficiently great and stable and controllable driving power to avoid drug blockage.

The invention discloses a unilateral-driven drug infusion device, comprising: a drug storage unit including a drug outlet; a screw connected to a piston and a driving wheel provided with wheel teeth, respectively, the driving wheel drives the screw to move by rotation, pushing the piston, provided in the drug storage unit, forward; at least one driving unit cooperating with the driving wheel, the driving unit includes at least one driving portion; a power unit and a reset unit connected to the driving unit, wherein: when the power unit outputs a force on the driving unit, the driving unit rotates around a pivot shaft, driving the driving portion to push the wheel teeth, thus rotating the driving wheel; when the reset unit outputs a force on the driving unit alone, the driving unit performs a reset rotation without the driving portion pushing the wheel teeth, thus making the driving wheel stop rotating; and an infusion tube, used as a drug infusion channel, includes a connection end and a subcutaneous end, and when the connection end is connected with the drug outlet and the subcutaneous end enters the subcutaneous, the drug is delivered subcutaneously through the infusion tube.

According to one aspect of this invention, the driving unit includes two driving portions, and under the cooperative operation of the power unit and the reset unit, the two driving portions can alternately push the wheel teeth.

According to one aspect of this invention, the two driving portions alternately push the wheel teeth disposed on the same driving wheel.

According to one aspect of the present invention, the driving wheel includes two sub-wheels provided with wheel teeth, and the two driving portions respectively alternately push the wheel teeth disposed on different sub-wheels.

According to one aspect of the invention, the power unit and the reset unit are linear actuators.

According to one aspect of the invention, the linear actuator includes a shape memory alloy.

According to one aspect of the present invention, the reset unit at least includes a spring, an elastic sheet, an elastic plate, an elastic rod, or elastic reset rubber.

According to one aspect of the present invention, the driving unit includes one driving portion, and the reset unit is a spring.

According to one aspect of the invention, the infusion tube includes a hard needle or a cannula.

According to one aspect of the invention, the infusion tube includes a hard needle and a cannula connected to each other, the connection end is a hard needle while the subcutaneous end is a cannula, or the connection end is a cannula while the subcutaneous end is a hard needle.

According to one aspect of the invention, both the connection end and the subcutaneous end are hard needles or cannulas.

According to one aspect of the present invention, it also includes an assembly structure, a part of the infusion tube is provided in the assembly structure, when the assembly structure is in the initial position, the connection end does not connect with the drug outlet, neither does the subcutaneous enter the subcutaneous, when the assembly structure is installed from the initial position to the working position, the connection end is connected with the drug outlet, and the subcutaneous end enters the subcutaneous.

According to one aspect of the invention, the subcutaneous end that is a cannula is manually pierced under the skin after the assembly structure is installed to the working position.

According to one aspect of the present invention, it further includes a transitional connection member which is disposed outside the drug outlet, and one end of the transitional connection member connects with the drug outlet, while the other end is used to connect the connection end.

According to one aspect of the present invention, the transitional connection member includes a connection cavity or a connection port.

Compared with the prior arts, the technical solution of the present invention has the following advantages:

In the unilateral-driven drug infusion device disclosed herein, at least one driving unit cooperating with the driving wheel, the driving unit includes at least one driving portion; a power unit and a reset unit connected to the driving unit, wherein: when the power unit outputs a force on the driving unit, the driving unit rotates around a pivot shaft, driving the driving portion to push the wheel teeth, thus rotating the driving wheel; when the reset unit outputs a force on the driving unit alone, the driving unit performs a reset rotation without the driving portion pushing the wheel teeth, thus making the driving wheel stop rotating. The power unit can provide a sufficiently great and stable driving power, which in turn enables the drug infusion device to have a sufficiently great and stable and controllable infusion pressure to avoid drug blockage and eliminate potential safety hazards.

Furthermore, the driving unit includes two driving portions, and under the cooperative operation of the power unit and the reset unit, the two driving portions can alternately push the wheel teeth. Two driving portions pushing the wheel teeth alternately can not only improve the infusion efficiency but also make the infusion device have multiple infusion modes.

Furthermore, the power unit and the reset unit are linear actuators. The force of the linear actuator can be controlled by current. When the current is constant, the force output by the linear actuator is constant. Therefore, the linear actuator can output stable and controllable force, thus making the drug infusion proceed smoothly.

Furthermore, the reset unit at least includes a spring, an elastic sheet, an elastic plate, an elastic rod, or an elastic reset rubber. When the reset unit is an elastic member, the reset unit can work without consuming additional energy, which reduces the power consumption of the drug infusion device and saves the production cost.

Furthermore, the infusion tube includes a hard needle or a cannula. Using hard needles can increase the strength of the infusion tube; using cannulas can increase the flexibility of the design of the infusion tube.

Furthermore, the transitional connection member includes a connection cavity or a connection port, avoiding drug leakage.

BRIEF DESCRIPTION OF THE DRAWINGS

FIG. 4b is the top view of FIG. 4a;

FIG. 8b is a schematic view of the driving unit in FIG. 8a;

DETAILED DESCRIPTION

As described above, the infusion device of the prior art has insufficient driving power for drug infusion, and it is prone to blockage, thereby having potential safety hazards.

The study found that the cause of the above problems is that the driving power for drug infusion is the resilience of the elastic member, but the resilience is prone to change and the stability is uncontrollable.

In order to solve this problem, the present invention provides a unilateral-driven drug infusion device, and the power unit drives the driving portion to push the wheel teeth forward. By controlling the current, the linear actuator can output a sufficiently great and stable and controllable driving power to avoid drug blockage.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

Figure 1:
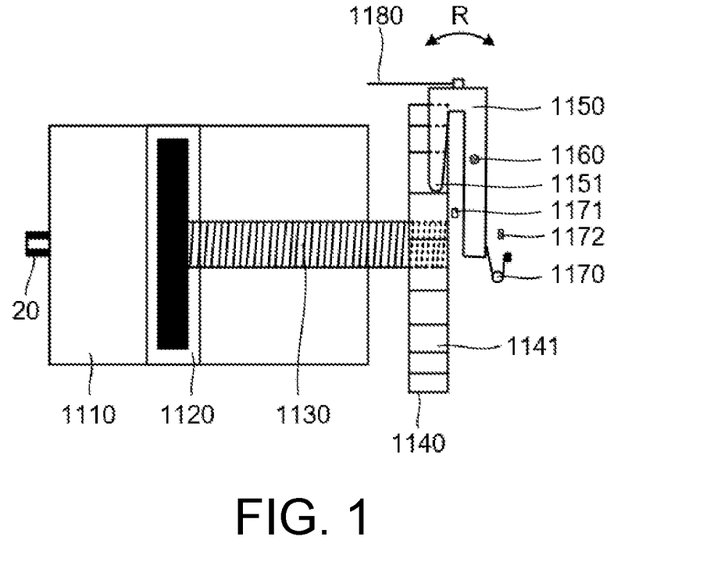
FIG. 1 is a schematic view of the main structures of the drug infusion device according to an embodiment of the present invention.

FIG. 1 is a schematic view of main structures in the infusion device according to an embodiment of the present invention.

The internal structure of the infusion device mainly includes a drug storage unit 1110, a piston 1120, a screw 1130, a driving wheel 1140, at least one driving unit 1150, a pivot shaft 1160, a reset unit 1170, a power unit 1180 and an infusion tube (not shown). The infusion tube will be described in detail below.

In the embodiment of this present invention, the driving unit 1150 is connected to the reset unit 1170 and the power unit 1180, respectively. It should be noted that the connection herein includes mechanical connection or electrical connection.

The drug storage unit 1110 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc. And the drug storage unit 1110 includes a drug outlet 20.

The piston 1120 is used to infuse liquid drug into the body.

The screw 1130 is connected to the piston 1120 and the driving wheel 1140, respectively. In the embodiment of the present invention, the driving wheel 1140 advances the screw 1130 forward by screwing, the screw 1130 then forces the piston 1120, arranged in the drug storage unit 1110, to move forward, so as to achieve the purpose of drug infusion.

The peripheral surface of the driving wheel 1140 is provided with wheel teeth 1141. The wheel teeth 1141 are gear teeth or ratchet teeth. Preferably, in the embodiment of the present invention, for improving driving efficiency, the wheel teeth 1141 are ratchet teeth which can be pushed more easily.

At least one driving portion 1151 is provided on the driving unit 1150 to push the wheel teeth 1141, thereby rotating the driving wheel 1140. The driving unit 1150 is movably connected to the pivot shaft 1160. Preferably, in the embodiment of the present invention, the driving unit 1150 includes a driving portion 1151.

The power unit 1180 and the reset unit 1170 cooperate with each other to make the driving unit 1150 rotate reciprocally around the pivot shaft 1160, as shown in the R direction in FIG. 1, thereby making the driving portion 1151 move in the advancing direction and reset direction. When the driving unit 1150 performs one reciprocating rotation, the driving wheel 1140 drives the screw 1130 forward one step, and the screw 1130 engages the piston 1120 to infuse one unit of drug.

It should be noted here that the advancing direction of the driving portion 1151 refers to the direction in which the wheel teeth 1141 moves, while the reset direction of the driving portion 1151 is opposite to the advancing direction. During the reset movement, the driving portion 1151 only slides on the surface of the wheel teeth 1141 without pushing them.

In some embodiments of the present invention, the reset unit 1170 at least includes a spring, an elastic piece, an elastic plate, an elastic rod, rubber and other elastic members. It should be noted that the spring herein includes a compression spring, an extension spring, or a torsion spring, etc. Preferably, the reset unit 1170 is a spring. Specifically, in the embodiment of the present invention, the reset unit 1170 is a torsion spring which is more conducive to the reset of the driving unit 1150. When the reset unit 1170 is an elastic member, it can work without consuming additional energy, which reduces the power consumption of the drug infusion device and saves the production cost.

In other embodiments of the present invention, the reset unit 1170 includes an electrically driven linear actuator or an electrically heated linear actuator, such as a shape memory alloy. After being energized, the physical form of the material of the linear actuator, like shape memory alloy, changes, which makes shrinkage deformation of the shape memory alloy occur, thereby outputting the driving force. The higher the current is, the larger the shrinkage deformation of the shape memory alloy occurs, and the greater the driving force outputs. Obviously, when the current is constant, the shrinkage deformation of the linear actuator is also constant, so the driving force is. Therefore, the shape memory alloy can output stable and controllable driving force for drug infusion.

The type, material selection or the position of the reset unit 1170 are not specifically limited herein, as long as it can satisfy the condition of making the driving unit 1150 rotate in the reset direction.

The power unit 1180 is an electrically driven linear actuator or an electrically heated linear actuator. By alternately turning on and off, the power unit 1180 outputs force in pulses. Specifically, in the embodiment of the present invention, the power unit 1180 is a shape memory alloy.

Figure 2A:
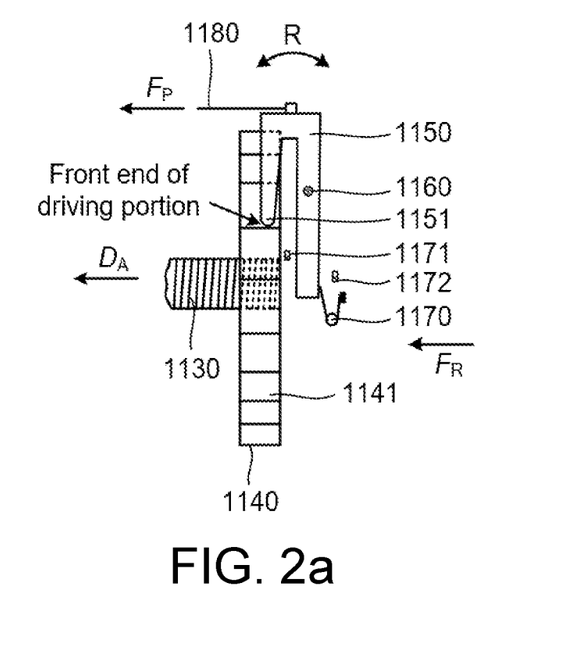
FIG. 2a-FIG. 2c are top views of the driving portion pushing the wheel teeth according to different embodiments of the present invention.
Figure 2B:
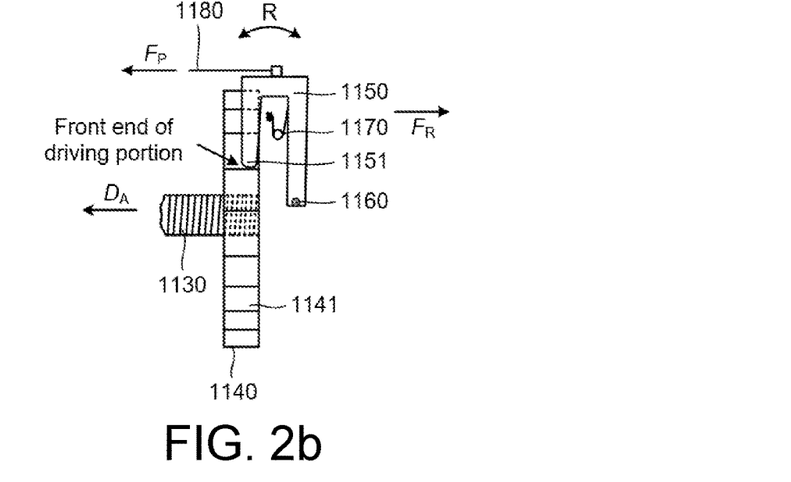
Figure 2C:
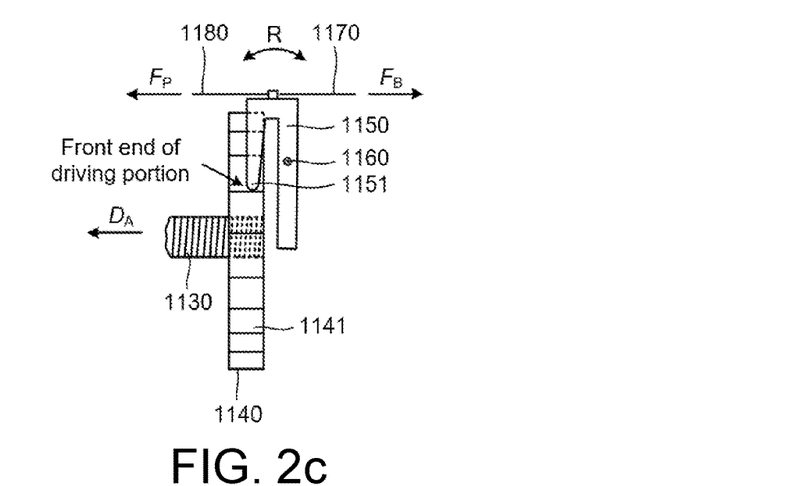
Figure 3A:
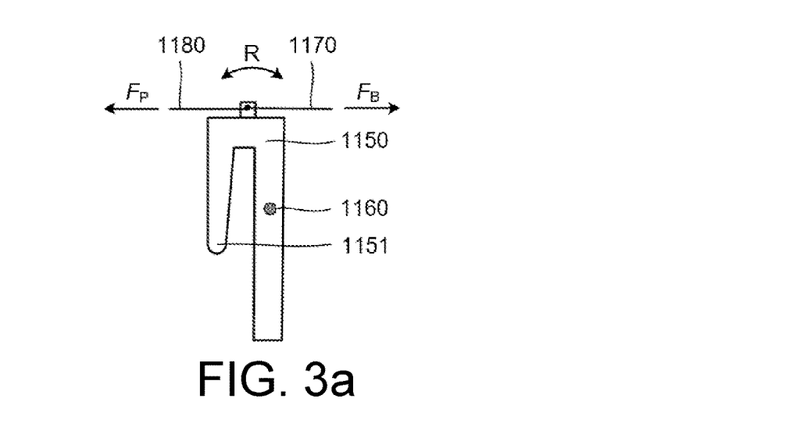
FIG. 3a-FIG. 3c are schematic views of the power unit, the reset unit and the driving unit cooperating with each other according to different embodiments of the present invention.
Figure 3B:
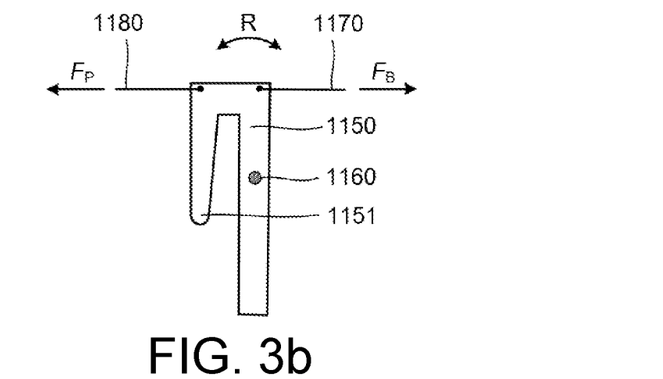
Figure 3C:
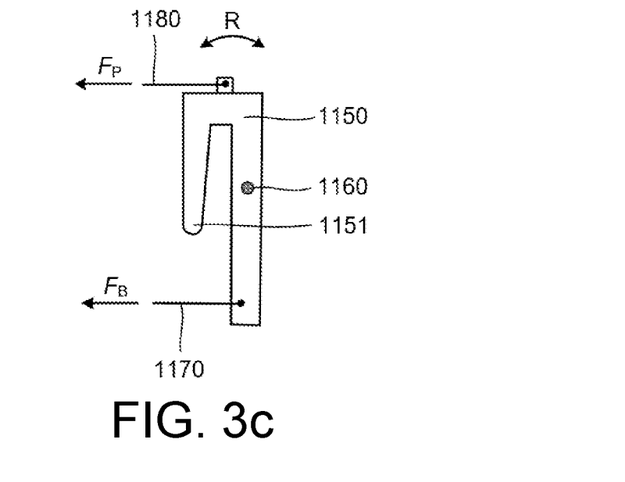

FIG. 2a-FIG. 2c are top views of the driving portion 1151 pushing the wheel teeth 1141 in different embodiments of the present invention. FIG. 3a-FIG. 3c are schematic views of the power unit 1180, the reset unit 1170 and the driving unit 1150 cooperating with each other in different embodiments of the present invention.

As shown in FIG. 2a and FIG. 2b, the principle of the reciprocating rotation of the driving unit 1150 in the embodiment of the present invention is as follows. When the power unit 1180 pulls the driving unit 1150 by force $F_p$, the driving unit 1150 rotates counter-clockwise (advancing direction) around the pivot shaft 1160, driving the driving portion 1151 to push the wheel teeth 1141 forward, and thereby making the driving wheel 1140 rotate. The driving wheel 1140 then moves the screw 1130 forward in $D_A$ direction. The reset unit 1170, as an elastic member, builds a gradually increasing elastic force $F_R$. When the power unit 1180 stops applying force and under the action of only the elastic force $F_R$, the driving unit 1150 will rotate clockwise (reset direction) around the pivot shaft 1160. At this time, the driving portion 1151 just slides on the surface of the wheel teeth 1141 instead of pushing them, therefore the driving wheel 1140 stops rotating. The driving unit 1150 completes one reciprocating rotation.

As shown in FIG. 2b, in another embodiment of the present invention, the reset unit 1170 and the power unit 1180 are disposed on the same side of the pivot shaft 1160. And according to the general technical principles, those skilled in the art can arbitrarily adjust the positional relationship and the connection relationship of the reset unit 1170, the driving unit 1150, and the power unit 1180, which is not specifically limited herein, as long as the above-mentioned rotation processes can be achieved.

As shown in FIG. 2c, in yet another embodiment of the present invention, the reset unit 1170 includes an electrically driven linear actuator or an electrically heated linear actuator, such as a shape memory alloy. Although the technical principle that the driving portion 1151 pushes the wheel teeth 1141 is consistent with the foregoing, the driving unit 1150 cannot automatically reset after the driving portion 1151 stops advancing, therefore, the reset unit 1170 is required to provide the reset force $F_B$ whose direction is opposite with that of $F_p$, thereby making the driving unit 1150 rotate reciprocally with the cooperation of the reset unit 1170 and the power unit 1180.

Preferably, as shown in FIG. 2a to FIG. 2c, in the embodiment of the present invention, the directions of $F_p$, $F_R$ (or $F_B$) and $D_A$ are parallel to one another. This parallel design can make full use of space and optimize the structural relationships inside the infusion device, making internal structure more compact.

Obviously, those skilled in the art can arbitrarily adjust the directions of the $F_p$ and $F_B$ as needed, as long as the conditions for reciprocating rotation of the driving unit 1150 are satisfied, as shown in FIG. 3a-FIG. 3c.

In other embodiments of the present invention, the direction of $F_p$ and the direction of $F_R$ (or $F_B$) or the direction of $D_A$ may not be parallel, which is not specifically limited herein, as long as the purpose of the reciprocating rotation of the driving unit 1150 can be achieved.

Figure 4A:
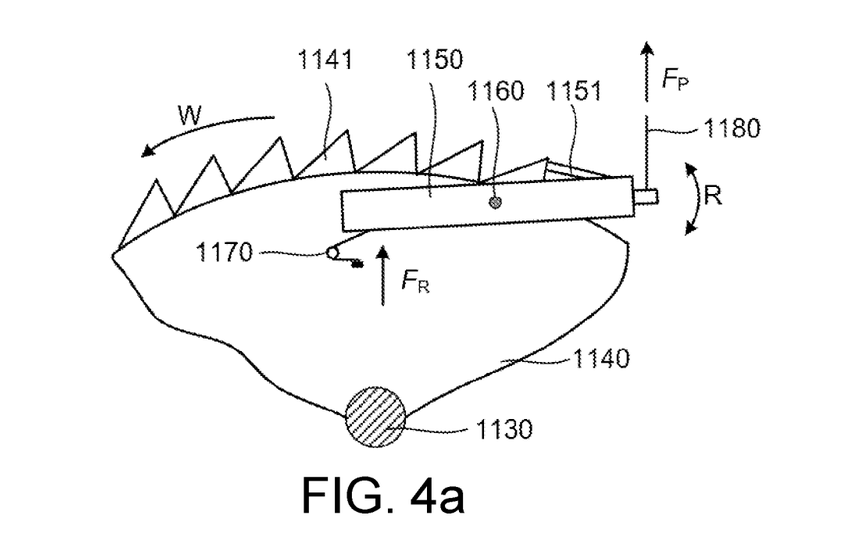
FIG. 4a-FIG. 4b are schematic views of that the pulling direction of the power unit is not parallel to the advancing direction of the screw according to another embodiment of the present invention.
Figure 4B:
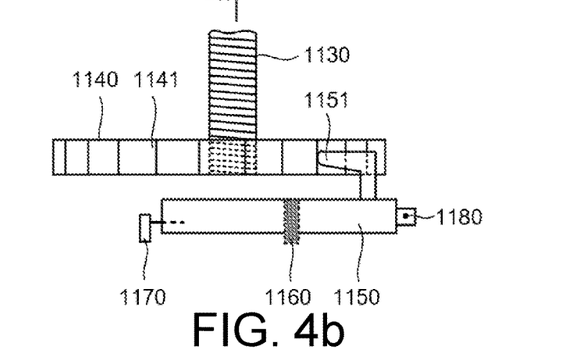

FIG. 4a-FIG. 4b are schematic views of that the pulling direction of the power unit 1180 is not parallel to the advancing direction of the screw 1130. FIG. 4b is the top view of FIG. 4a.

The $F_p$ direction of the power unit 1180 is perpendicular to the forward direction $D_A$ of the screw 1130. The pivot shaft 1160 and the reset unit 1170 are disposed on the base. As described above, the driving unit 1150, rotating reciprocally in the R direction, drives the driving portion 1151 to push the wheel teeth 1141, making the driving wheel 1140 rotate in the W direction and driving the screw 1130 to advance in the $D_A$ direction. The driving principle of the driving unit 1150 is consistent with the foregoing embodiment.

In the embodiment of the present invention, blocking walls 1171 and 1172 (as shown in FIG. 1 and FIG. 2a) that can stop the driving unit 1150 from rotating are also provided in the infusion device. And an electrical signal may be triggered when the driving unit 1150 contacts the blocking wall 1171 or 1172, allowing the program unit to control the driving force output of the power unit 1180. In another embodiment of the present invention, only the blocking wall 1171 or only the blocking wall 1172 may be provided, so that the rotating terminal in either direction of the driving unit 1150 is controlled by the program unit. The position of the blocking wall 1171 or 1172 is not specifically limited herein, as long as the condition that the driving unit 1150 stops rotating can be satisfied.

In another embodiment of the present invention, no blocking wall is provided (as shown in FIG. 2b to FIG. 4b), and the rotating terminal of the driving unit 1150 is completely controlled by the program unit.

Figure 5:
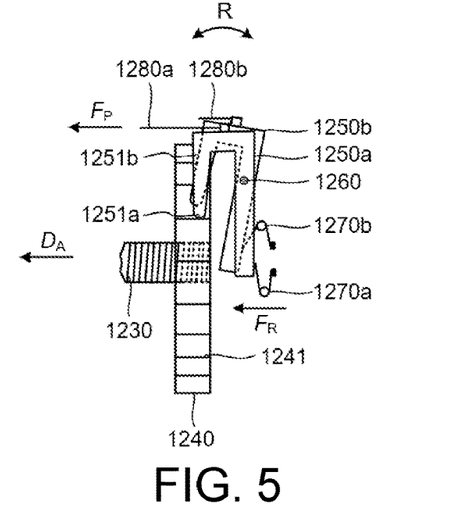
FIG. 5 is a schematic view of a driving unit including two driving units according to an embodiment of the present invention.
Figure 6:
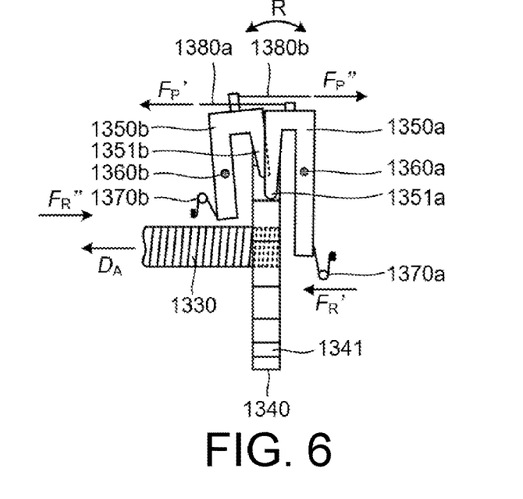
FIG. 6 is a schematic view of a driving unit including two driving units according to another embodiment of the present invention.

FIG. 5 and FIG. 6 are schematic views of a driving unit including two driving units according to different embodiments of the present invention.

As shown in FIG. 5, the driving unit 1250a rotates reciprocally in the R direction around the pivot shaft 1260 under the action of the linear actuator 1280a and the reset unit 1270a. Similarly, the driving unit 1250b rotates reciprocally in the R direction around the pivot shaft 1260 under the action of the linear actuator 1280b and the reset unit 1270b. In the embodiment of the present invention, the reciprocating rotations of the two driving units do not interfere with each other. Therefore, both the driving unit 1250a and the driving unit 1250b can independently implement the driving method or principle described above.

Preferably, in the embodiment of the present invention, the driving unit 1250a and the driving unit 1250b rotate asynchronously. That is, when the driving portion 1251a of the driving unit 1250a pushes the wheel teeth 1241 to move, the driving portion 1251b of the driving unit 1250b slides on the surface of the wheel teeth 1241. When the driving portion 1251b slides to one position, the program unit controls the linear actuator 1280a to stop outputting driving power to the driving unit 1250a, and in turn controls the linear actuator 1280b to output power to the driving unit 1250b. At this time, the driving unit 1250a rotates in the clockwise direction under the action of the reset unit 1270a, and the driving portion 1251a slides on the surface of the wheel teeth, while the driving portion 1251b pushes the wheel teeth 1241. The driving units 1250a and 1250b are alternately powered to push the same driving wheels 1240.

In the embodiment of the present invention, the pulling force $F_p$ of the linear actuators 1280a and 1280b, the elastic force $F_R$ of the reset units 1270a and 1270b and the forward direction $D_A$ of the screw 1230 are shown in the figures. Like foregoing statement, the direction of the pulling force $F_p$ is parallel to the forward direction $D_A$ of the screw 1230. Two driving portions pushing the wheel teeth alternately can not only improve the infusion efficiency, but also make the infusion device have multiple infusion modes.

In the embodiment of the present invention, the types of the reset units 1270a and 1270b can be referred to the above, which will not be repeated herein.

As shown in FIG. 6, the driving portions 1351a and 1351b alternately push the wheel teeth 1341, respectively, and the force output by the linear actuators 1380a and 1380b are both controlled by the program unit.

It should be noted that, in the embodiment of the present invention, the direction of the pulling force $F_p'$ of the linear actuator 1380a and that of the pulling force $F_p''$ of the linear actuator 1380b are opposite. Obviously, the direction of the resetting force $F_R'$ of the reset unit 1370a and that of the resetting force $F_R''$ of the reset unit 1370b are also opposite.

Also, in the embodiment of the present invention, the driving units 1350a and 1350b rotate asynchronously. That is, when the driving portion 1351a of the driving unit 1350a pushes the wheel teeth 1341 forward, the driving portion 1351b of the driving unit 1350b slides on the surface of the wheel teeth 1341. When the driving portion 1351b slides to one position, the program unit controls the linear actuator 1380a to stop outputting power to the driving unit 1350a, and in turn controls the linear actuator 1380b to output power to the driving unit 1350b. The driving unit 1350a resets to the clockwise rotation by the reset unit 1370a, while the driving portion 1351a slides on the surface of the wheel teeth 1341, and the driving portion 1351b pushes the wheel teeth 1341. The driving units 1350a and 1350b alternately pushes the driving wheels 1340.

Similarly, both the driving unit 1350a and the driving unit 1350b can independently implement the driving method or principle described above. And the types of the reset units 1370a and 1370b can be referred to the above, which will not be repeated herein.

It should be noted that, in other embodiments of the present invention, more driving units can be arranged in the driving unit, or more driving portions are disposed on each driving unit, or the driving wheel includes more sub-wheels. Therefore, different driving units respectively push the corresponding sub-wheel to rotate.

Figure 7A:
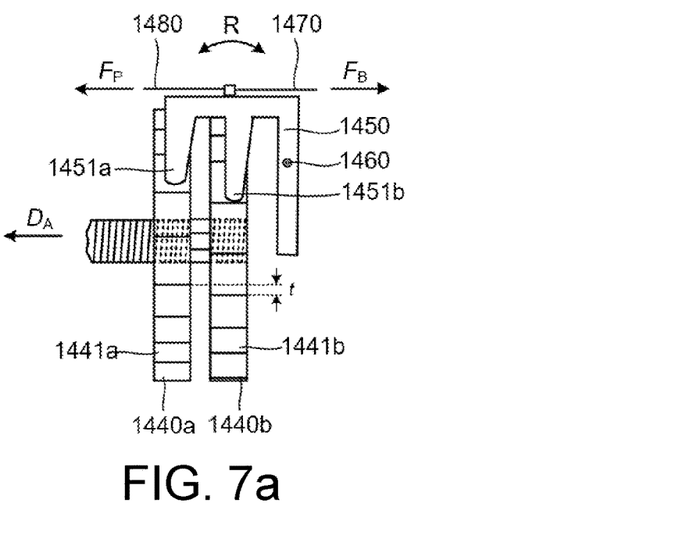
FIG. 7a-FIG. 7b are schematic views of two driving portions of one driving unit cooperating with two sub-wheels respectively according to yet another embodiment of the present invention.
Figure 7B:
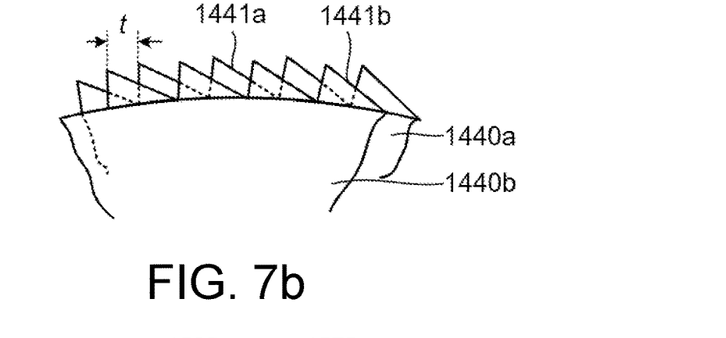

FIG. 7a and FIG. 7b are schematic views of two driving portions 1451a and 1451b of a driving unit 1450 cooperating with two sub-wheels 1440a and 1440b, respectively according to yet another embodiment of the present invention. FIG. 7b is a right view of the partial teeth structure of the sub-wheels 1440a and 1440b in FIG. 7a.

As shown in FIG. 7a and FIG. 7b, in the embodiment of the present invention, the driving unit 1450 includes two driving portions 1451a and 1451b disposed left and right, while the driving wheel includes two fixedly connected sub-wheels 1440a and 1440b disposed on the left and right (that is, two sub-wheels can move simultaneously). The driving portions 1451a and 1451b cooperate with the sub-wheels 1440a and 1440b, respectively, and the pivot shaft 1460 is disposed on the same side of two sub-wheels 1440a and 1440b. Both the linear actuator 1480 and the reset unit 1470 of the embodiment of the present invention are shape memory alloys, and the driving portion 1451a or 1451b can respectively push the wheel teeth 1441a or 1441b forward. Their working principles and operating modes are consistent with the foregoing embodiments.

In addition to driving portion 1451a or 1451b operating independently, the embodiment of the present invention can also adjust the distance between the front ends of the driving portions 1451a and 1451b, or adjust the offset degree of the wheel teeth 1441a and 1441b to make two driving portions 1451a and 1451b cooperate with each other. Preferably, in the embodiment of the present invention, the wheel teeth 1441a and 1441b are offset with degree t, as shown in FIG. 7a and FIG. 7b.

Obviously, in the embodiment of the present invention, two driving portions 1451a and 1451b reciprocate synchronously. As shown in FIG. 7a, when the previous forward movement is completed, the driving unit 1450 starts a reset rotation, the driving portion 1451a reaches the driving position before the driving portion 1451b, so the driving portion 1451a can be used to start the next forward movement instead. Or the driving unit 1450 continues the reset movement until the driving portion 1451b reaches the next driving position to start the next forward movement.

Figure 8A:
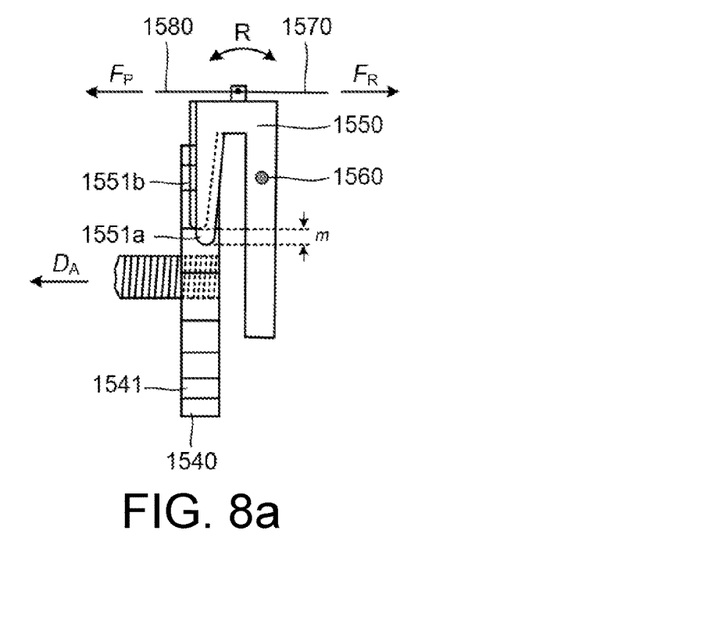
FIG. 8a-FIG. 8b are schematic views of two driving portions of one driving unit cooperate with the same driving wheel according to yet another embodiment of the present invention.
Figure 8B:
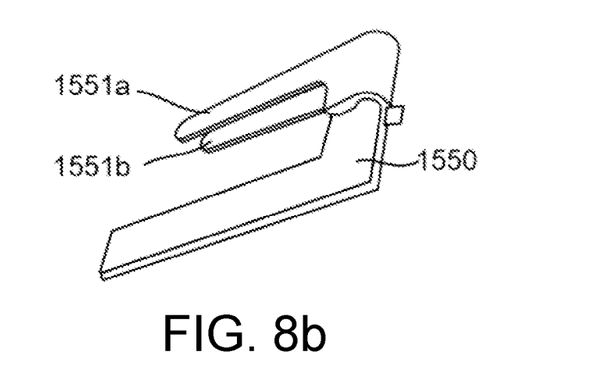

FIG. 8a and FIG. 8b are still another embodiment of the present invention in which the driving unit 1550 includes two driving portions 1551a and 1551b disposed up and down, and driving portions 1551a and 1551b cooperate with the same driving wheel 1540. FIG. 8b is a schematic view of the driving unit 1550 in FIG. 8a.

As shown in FIG. 8a and FIG. 8b, the driving unit 1550 includes two driving portions 1551a and 1551b disposed up and down cooperating with the same driving wheel 1540, so the driving portions 1551a and 1551b reciprocate synchronously. The front ends of the driving portions 1551a and 1551b are not level with a certain distance m, therefore, the two cannot simultaneously push the wheel teeth 1541 forward, as shown in FIG. 8a. When the driving portion 1551b finishes the last forward movement, the driving unit 1550 performs a reset movement, obviously making the driving portion 1551a reach the next driving position before the driving portion 1551b. The driving portion 1551a can be used to push the wheel teeth 1541 forward to start the next forward movement.

In other embodiments of the present invention, the driving unit may further include more driving portions, such as 3, 4 or more, which is not specifically limited herein.

Figure 9A:
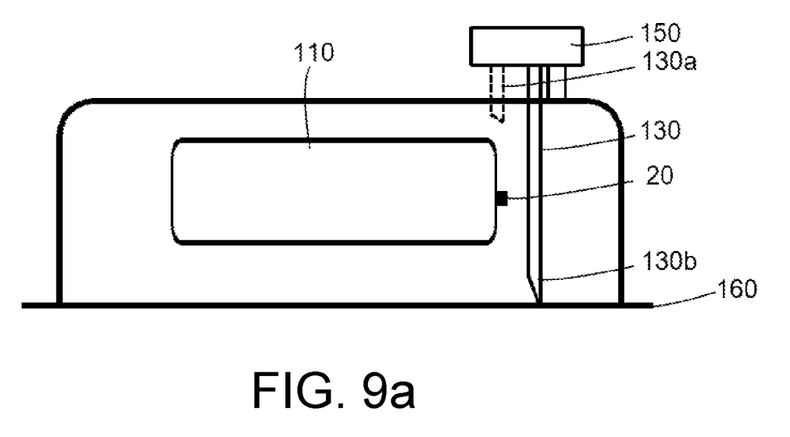
FIG. 9a is a schematic view of an assembly structure of a unilateral-driven drug infusion device in an initial position according to one embodiment of the present invention.
Figure 9B:
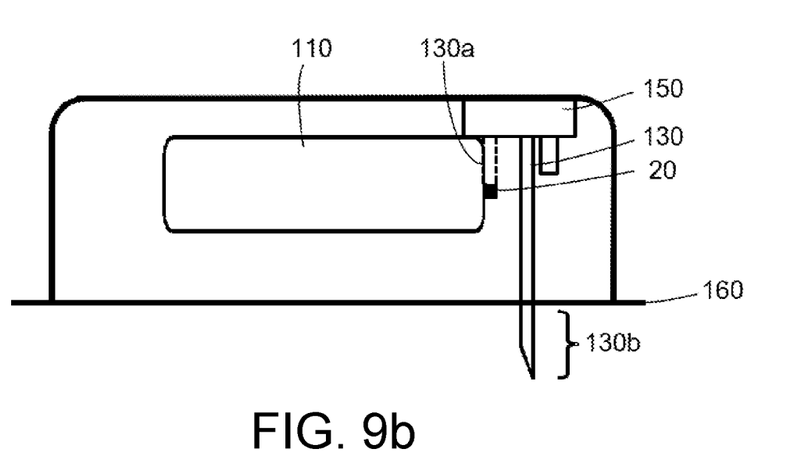
FIG. 9b is a schematic view of an assembly structure of a unilateral-driven drug infusion device in a working position according to an embodiment of the present invention.
Figure 9C:
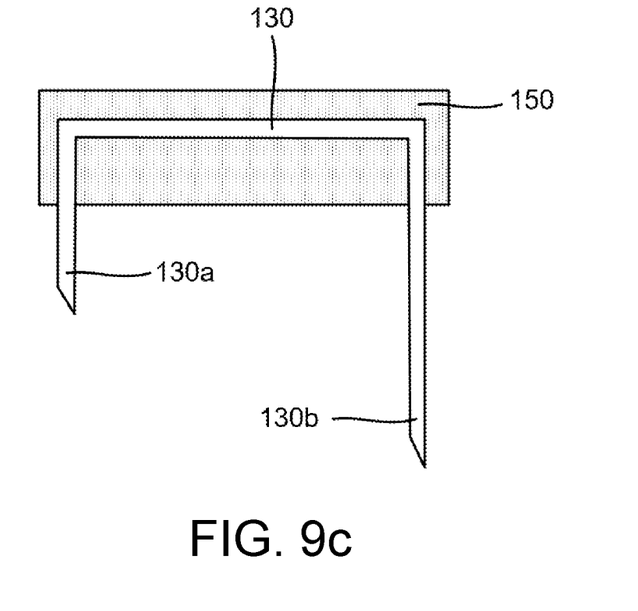
FIG. 9c is a schematic view of the infusion tube provided in an assembly structure according to an embodiment of the present invention.

FIG. 9a-FIG. 9b are schematic views of the assembly structure 150 of an infusion device in the initial position and the working position according to an embodiment of the present invention. FIG. 9c is a schematic view of part of the infusion tube 130 disposed in the assembly structure 150 according to an embodiment of the present invention.

As described above, the infusion device of the embodiment of the present invention further includes an infusion tube 130 which is used as the drug infusion channel. The infusion tube 130 includes a connection end 130a and a subcutaneous end 130b. When the connection end 130a connects the drug outlet 20 and the subcutaneous end 130b enters the subcutaneous, the drug can be delivered to the subcutaneous through the infusion tube 130.

It should be noted that there are various manners in which the connection end 130a connects the drug outlet 20, or in which the subcutaneous end 130b enters the subcutaneous, or the order of the two steps may be different, which is not specifically limited herein.

The infusion tube 130 includes a hard needle or a cannula. Using hard needle can increase the strength of the infusion tube 130. Using the cannula can increase the flexibility of the design of the infusion tube 130. Specifically, in the embodiment of the present invention, the entire infusion tube 130 is a hard needle or a cannula.

In yet another embodiment of the present invention, the infusion tube 130 includes a hard needle and a cannula connected with each other. That is, the infusion tube 130 includes multiple parts. For example, the connection end 130a is a hard needle while the subcutaneous end 130b is a cannula; or the connection end 130a is a cannula while the subcutaneous end 130b is a hard needle, which improves the flexibility of the infusion device structure design.

In another embodiment of the present invention, both the connection end 130a and the subcutaneous end 130b are hard needles or cannulas. At this time, the portion connecting the connection end 130a and the subcutaneous end 130b may be a hard needle or a cannula, or a closed structure with a cavity, that is, the connection end 130a, the subcutaneous end 130b and this said portion here make up the infusion tube 130, which is not specifically limited herein.

In the embodiment of the present invention, the infusion device further includes an assembly structure 150. A part of the infusion tube 130 is provided in the assembly structure 150, as shown in FIG. 9c. While in the initial position, the assembly structure 150 protrudes from the surface of the infusion device case, and the connection end 130a does not connect with the drug outlet 20, neither does the subcutaneous end 130b enter the subcutaneous, as shown in FIG. 9a. While installed from the initial position to the working position, the assembly structure 150, the top of which is integrated with the infusion device case, enters the infusion device, and the connection end 130a connects the drug outlet 20, and the subcutaneous end 130b enters the subcutaneous, as shown in the FIG. 9b. Obviously, in the embodiment of the present invention, the assembly structure 150 supports the infusion tube 130 to move synchronously as a whole.

Before using, the assembly structure 150 carries the infusion tube 130 in the initial position. When the infusion device is attached on the surface of the human body by the medical adhesive tape 160, the assembly structure 150 is pressed to complete the installation operation, so the infusion tube 130 becomes a bridge connecting the body fluid and the drug storage unit 1110, and the infusion device can start working normally. Compared with other installation methods, the installation method of the embodiment of the present invention reduces the user's operation steps during installation, making the installation more convenient and flexible, and improving the user experience.

The infusion tube 130 can be arranged in the assembly structure 150 in various ways, which is not specifically limited herein. In another embodiment of the present invention, the assembly structure 150 can be controlled to be automatically, not manually, installed from the initial position to the working position.

In another embodiment of the present invention, the subcutaneous end 130b is a cannula. After the assembly structure 150 is installed in the working position, the subcutaneous end 130b is manually penetrated by the user. In yet another embodiment of the present invention, the subcutaneous end 130b is a cannula. The user can pierce the subcutaneous end 130b under the skin firstly, and then install the assembly structure 150 to the working position, thus helping the connection end 130a connect the drug outlet 20.

It should be noted that in other embodiments of the present invention, the assembly structure 150 may not be provided, but the infusion tube 130 is directly fixedly installed in the infusion device. While the infusion device is attached to the skin, the subcutaneous end 130b penetrates under the skin synchronously.

Figure 10:
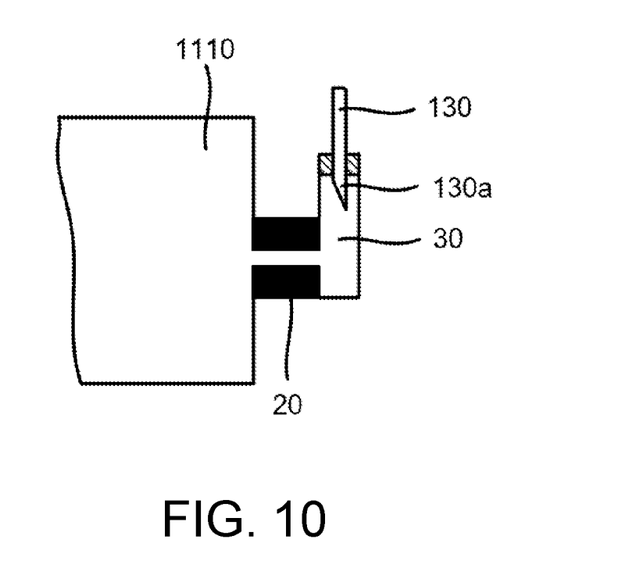
FIG. 10 is a schematic view of the drug outlet, the transitional connection member and the infusion tube according to an embodiment of the present invention.

FIG. 10 is a schematic view of the drug outlet 20, the transitional connection member 30, and the infusion tube 130 connected with each other according to an embodiment of the present invention.

The embodiment of the present invention further includes a transitional connection member 30. The transitional connection member 30, one end of which is connected with the drug outlet 20, is disposed outside the drug outlet 20. In some embodiments of the present invention, since the infusion tube 130 is not always connected with the drug outlet 20, the transitional connection member 30 can prevent the drug from leaking. Preferably, in the embodiment of the present invention, the transitional connection member 30 is a connection cavity. When the assembly structure 150 is installed to the working position, the connection end 130a enters the connection cavity to achieve connection with the drug outlet 20.

In another embodiment of the present invention, the transitional connection member 30 is a connection port. When the assembly structure 150 is installed to the working position, the connection end 130a is connected to the connection port to achieve connection with the drug outlet 20.

It should be noted that the transitional connection member 30 is a part of the drug storage unit 1110 or a separate structure, which is not specifically limited herein.

In summary, the present invention provides a unilateral-driven drug infusion device, in which the power unit drives the driving portion to push the wheel teeth forward. By controlling the current, the power unit can output a sufficiently great and stable and controllable driving power to avoid drug blockage.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A unilateral-driven drug infusion device, comprising:
   a drug storage unit, including a drug outlet;
   a screw, connected to a piston and a driving wheel provided with wheel teeth, respectively, wherein the driving wheel drives the screw to move by rotation, so as to push the piston provided in the drug storage unit to move forward;
   at least one driving unit, cooperating with the driving wheel, wherein the driving unit includes at least one driving portion;
   a power unit and a reset unit, connected to the driving unit, wherein
      when the power unit outputs a force on the driving unit, the driving unit rotates around a pivot shaft, the driving portion pushes the wheel teeth, and the driving wheel rotates;
      when the reset unit outputs a force on the driving unit alone, the driving unit performs a reset rotation without the driving portion pushing the wheel teeth, and the driving wheel stops rotating;
   and,
   an infusion tube, configured as a drug infusion channel and including a connection end and a subcutaneous end, wherein when the connection end is communicated with the drug outlet and the subcutaneous end enters a skin, the drug is delivered subcutaneously through the infusion tube.

2. The unilateral-driven drug infusion device of claim 1, wherein
   the driving unit includes two driving portions, and under cooperative operation of the power unit and the reset unit, the two driving portions can alternately push the wheel teeth.

3. The unilateral-driven drug infusion device of claim 2, wherein
   the two driving portions alternately push the wheel teeth disposed on the same driving wheel.

4. The unilateral-driven drug infusion device of claim 2, wherein
   the driving wheel includes two sub-wheels provided with wheel teeth, and the two driving portions respectively alternately push the wheel teeth disposed on different sub-wheels.

5. The unilateral-driven drug infusion device of claim 1, wherein
   the power unit and the reset unit are linear actuators.

6. The unilateral-driven drug infusion device of claim 5, wherein
   each of the linear actuators includes a shape memory alloy.

7. The unilateral-driven drug infusion device of claim 1, wherein
   the reset unit at least includes a spring, an elastic sheet, an elastic plate, an elastic rod, or elastic reset rubber.

8. The unilateral-driven drug infusion device of claim 7, wherein
   the driving unit includes one driving portion, and the reset unit is a spring.

9. The unilateral-driven drug infusion device of claim 1, wherein
   the infusion tube includes a hard needle or a cannula.

10. The unilateral-driven drug infusion device of claim 9, wherein
    the infusion tube includes the hard needle and the cannula connected to each other, the connection end is the hard needle while the subcutaneous end is the cannula, or the connection end is the cannula while the subcutaneous end is the hard needle.

11. The unilateral-driven drug infusion device of claim 10, further comprising an assembly structure, wherein
    a part of the infusion tube is provided in the assembly structure, when the assembly structure is in an initial position, the connection end does not communicate with the drug outlet, and the subcutaneous end does not enter the skin, when the assembly structure is installed from the initial position to a working position, the connection end is communicated with the drug outlet, and the subcutaneous end enters the skin.

12. The unilateral-driven drug infusion device of claim 11, wherein
    the subcutaneous end that is the cannula is manually pierced under the skin when the assembly structure is installed to the working position.

13. The unilateral-driven drug infusion device of claim 1, further comprising a transitional connection member, wherein
    the transitional connection member is disposed outside the drug outlet, and one end of the transitional connection member communicates with the drug outlet, while the other end of the transitional connection member is used to communicate the connection end.

14. The unilateral-driven drug infusion device of claim 13, wherein the transitional connection member includes a connection cavity or a connection port.

* * * * *